United States Patent [19]

Sokol et al.

[11] Patent Number: 5,652,111
[45] Date of Patent: Jul. 29, 1997

[54] BINDING ASSAY UTILIZING A NUCLEIC ACID ENCODING APAMIN BINDING PROTEIN

[75] Inventors: Patricia Tyson Sokol, Bedminster; Mohammad Reza Ziai, Montvale, both of N.J.

[73] Assignee: American Cyanamid Company, Parsippany, N.J.

[21] Appl. No.: 436,716

[22] Filed: May 8, 1995

Related U.S. Application Data

[62] Division of Ser. No. 314,979, Sep. 29, 1994, which is a continuation of Ser. No. 923,095, Jul. 30, 1992, Pat. No. 5,401,652.

[51] Int. Cl.$^6$ .............................. C12Q 1/68; C12N 5/10
[52] U.S. Cl. ........................... 435/7.1; 435/6; 435/69.1; 435/252.3; 435/320.1; 536/23.5
[58] Field of Search ........................... 435/7.1, 7.2, 69.1, 435/252.3, 6; 436/501

[56] References Cited

PUBLICATIONS

Rudy, B., "Diversity and Ubiquity of K Channels," *Neuroscience*, 25:729–749 (1988).
Castle, N. A., et al., "Toxins in the Characterization of Potassium Channels," *TINS*, 12:59–65 (1989).
Haylett, B. G. et al., "Calcium–activated Potassium Channels," In Cook, N.S. (ed.), Ellis Horwood Ltd., 70–95 (1990).
Latorre, R., et al., "Varieties of Calcium–Activated Potassium Channels," *Annu. Rev. Physiol.*, 51:385–399 (1989).
Pennefather, P., et al., "Two Distinct Ca–Dependent K Currents in Bullfrog Sympathetic Ganglion Cells," *Proc. Natl. Acad. Sci., USA*, 82:3040–3044 (1985).
Marty, A., "The Physiological Role of Calcium–Dependent Channels," *TINS*, 12:420–424 (1989).
Lancaster, B., et al., "Calcium Activates Two Types of Potassium Channels in Rat Hippocampal Neurons in Culture," *J. Neurosci.*, 11:23–30 (1991).
Strong, P. N., "Potassium Channel Toxins," *Pharmac. Ther.*, 46:137–162 (1990).
Saunders, H. H., et al., "Spontaneous Transient Outward Currents and CA++–Activated K+ Channels in Swine Tracheal Smooth Muscle Cells," *J. Pharmacol. Exp. Ther.*, 257:1114–1119 (1991).
Moczydlowski, E. et al., "An Emerging Pharmacology of Peptide Toxins Targeted Against Potassium Channels," *J. Membrane Biol.*, 105:95–111 (1988).
Blatz, A. L. et al., "Ion Conductance and Selectivity of Single Calcium–activated Potassium Channels in Cultured Rat Muscle," *J. Gen. Physiol*, 84:1–23 (1984).
Blatz, A. L., et al., "Single Apamin–blocked Ca–activated K+ Channels of Small Conductance in Cultured Rat Skeletal Muscle," *TINS*, 10:463–467 (1987).
Blatz, A. L., et al., "Calcium–Activated Potasiium Channels," *TINS*,10:463–467 (1987).

Habermann, E., et al., "Bee Venom Neurotoxin (Apamin): Iodine Labeling and Characterization of Binding Sites," *Eur. J. Biochem.*, 94:355–364 (1979).
Mourre, C., et al., "Quantitative Autoradiographic Mapping in Rat Brain of the Receptor of Apamin, a Polypeptide Toxin Specific for One Class of CA2+–Dependent K+ Channels," *Brain Res.*, 382:239–249 (1986).
Seagar, M. J., et al., "Molecular Structure of Rat Brain Apamin Receptor: Differential Photoaffinity Labeling of Putative K+ Channel Subunits and Target Size Analysis," *Biochemistry*, 25:4051–4057 (1986).
Seagar, M. J., et al., "Solubilization of the Apamin Receptor Associated with a Calcium–Activated Potassium Channel From Rat Brain," *J. Neurosci.*, 7:565–570 (1987).
Schmid–Antomarchi, H., et al., "Molecular Properties of the Apamin–binding Component of the CA2+–dependent K+ Channel," *Eur. J. Biochem.*, 142:1–6 (1984).
Wu, K., et al., "Existence of a CA2+–Dependent K+ Channel in Synaptic Membrane and Postsynaptic Density Fractions Isolated from Canine Cerebral Cortex and Cerebellum, as Determined by Apamin Binding," *Brain Res.*, 360:183–194 (1985).
Seagar, M. J., et al., "Photoaffinity Labeling of Components of the Apamin–sensitive K+ Channel in Neuronal Membranes," *J. Biol. Chem.*, 260:3895–3898 (1985).
Leveque, C., et al., "Polypeptide Components of the Apamin Receptor Associated with a Calcium Activated Potassium Channel," *FEBS Letters*, 275:185–189 (1990).
Marqueze, B., et al., "Photoaffinity Labeling of the K+–Channel Associated Apamin–Binding Molecule in Smooth Muscle, Liver and Heart Membranes," *Eur. J. Biochem.*, 169:295–298 (1987).
Ziai, M. R., et al., "Analysis with Monoclonal Antibodies of the Molecular and Cellular Heterogeneity of Human High Molecular Weight Melanoma Associated Antigen," *Cancer Res.*, 47:2474–2480 (1987).
Ziai, M. R., et al., "An Enzyme–Linked Double Antibody Immunoassay to Measure Muring Immunoglobulins—Its Application to Determine the Specific Activity of Radiolabeled Monoclonal Antibodies," *J. Immunol. Methods*, 82:233–241 (1985).
Hayashibe, K., et al., "A Heterogeneous Double Antibody Enzyme–Linked Immunoassay to Measure β–Galactosidase Fusion Protein," *J. Immunoassay*, 11:89–95 (1990).
Staros, J. V., et al., "Enhancement by N–Hydroxysulfosuccinimide of Water–Soluble Carbodimide–Mediated Coupling Reactions," *Analyt. Biochem.*, 156:220–222 (1986).

(List continued on next page.)

*Primary Examiner*—John Ulm
*Attorney, Agent, or Firm*—Hamilton, Brook, Smith & Reynolds, P.C.

[57] ABSTRACT

The present invention relates to an isolated nucleic acid fragment comprising a nucleic acid sequence encoding an apamin receptor protein, or biologically active fragment thereof.

4 Claims, 9 Drawing Sheets

OTHER PUBLICATIONS

Cornett, W. C., et al., "Specificity of Monoclonal Antibodies Reactive with Fusobacterium Nucleatum: Effect of Formalin Fixation," *J. Immunol. Methods*, 84:321–326 (1985).

Lu, et al., "CA2+–activated K+ Channels from Rabbit Kidney Medullary Thick Ascending Limb Cells Expressed in Xenopus Oocytes," *J. Biol. Chem.*, 265:16190–16194 (1990).

Wang, W., "Renal Potassium Channels and Their Regulation," *Annu. Rev. Physiol.*, 54:81–96 (1992).

Atkinson, N. S., et al., "A Component of Calcium–Activated Potassium Channels Encoded by the Drosophila Slo Locus," *Science*, 253:551–555 (1991).

Daniel, S., et al., "Screening for Potassium Channel Modulators by a High Through–Put 86–Rubidium Efflux Assay in a 96–Well Microtiter Plate," *J. Pharmacol Methods*, 25;185–193 (1991).

Messier, C., et al., "Effect of Apamin, a Toxin that Inhibits CA2+–dependent K+ Channels, On Learning and Memory Processes," *Brain Res.*, 551:322–326 (1991).

Fosset, Michel, et al., "The presence in pig brain of an endogenous equivalent of apamin, the bee venom peptide that specifically blocks $Ca^{2+}$–dependent $K^+$ channels", *Proc. Natl. Acad. Sci. USA*, 81:7228–7232 (1984).

Lee, Cheng Chi, et al., "Generation of cDNA Probes Directed by Amino Acid Sequence: Cloning of Urate Oxidase", *Science*, 239:1288–1291 (1988).

Sokol, Patricia T., et al., "Cloning of an Apamin Binding Protein of Vascular Smooth Muscle", *Journal of Protein Chemistry*, 13(1):117–128 (1994).

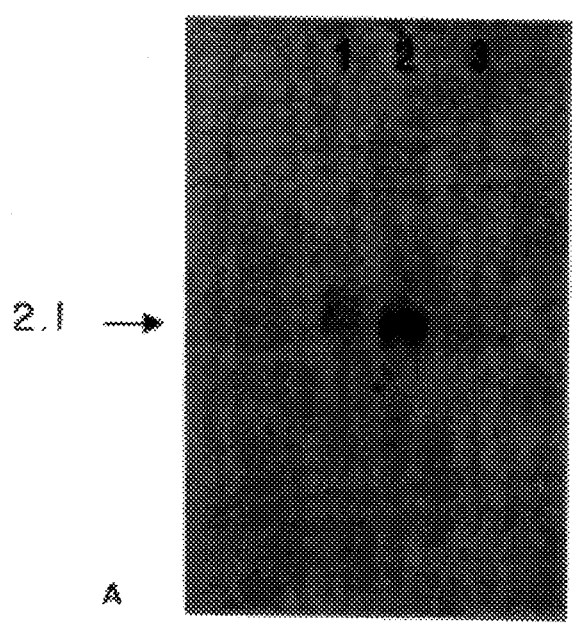
FIG. IA
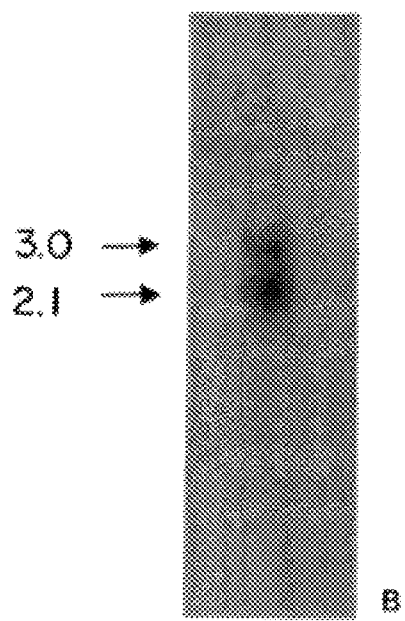
FIG. IB

```
     agcagctccataggcccagccccggcgtacaaggatcacttccggtggtacttcactacc
1    ---------+---------+---------+---------+---------+---------+   60
     tcgtcgaggtatccgggtcggggccgcatgttcctagtgaaggccaccatgaagtgatgg aagaagctgcgattgggcgagcgtggaaggggcatttccggtgtccacctgcttgggttc
61   ---------+---------+---------+---------+---------+---------+   120
     ttcttcgacgctaacccgctcgcaccttccccgtaaaggccacaggtggacgaacccaag tttggacagaagtaggaagATGGAGCTCGGCGCCGCGGCCCGTGCTTGGTCGCTCTTGTG
121  ---------+---------+---------+---------+---------+---------+   180
     aaacctgtcttcatccttcTACCTCGAGCCGCGGCGCCGGGCACGAACCAGCGAGAACAC M  E  L  G  A  A  A  R  A  W  S  L  L  W
                                                    ‾‾‾‾‾‾‾‾‾‾‾‾‾

GCTGCTGCTTCCCTTGCTTGGCCTGGTCGGCGCCAGCGGTCCCCGTACCTTAGTGCTTCT
181  ---------+---------+---------+---------+---------+---------+   240
     CGACGACGAAGGGAACGAACCGGACCAGCCGCGGTCGCCAGGGGCATGGAATCACGAAGA

L  L  L  P  L  L  G  L  V  G  A  S  G  P   R  T  L  V  L  L
     ‾‾‾‾‾‾‾‾‾‾‾‾‾‾‾‾‾‾‾‾‾‾‾‾‾‾‾‾‾‾‾‾‾‾‾‾‾‾‾‾‾‾

GGACAACCTCAACCTGCGGGAGACGCATTCACTTTTCTTCCGGAGCCTAAAGGATCGGGG
241  ---------+---------+---------+---------+---------+---------+   300
     CCTGTTGGAGTTGGACGCCCTCTGCGTAAGTGAAAAGAAGGCCTCGGATTTCCTAGCCCC

D  N  L  N  L  R  E  T  H  S  L  F  F  R  S  L  K  D  R  G

CTTCGTACTCACATTCAAGACCGCAGATGACCCCAGCCTGTCCCTGATTAAGTACGGAGA
301  ---------+---------+---------+---------+---------+---------+   360
     GAAGCATGAGTGTAAGTTCTGGCGTCTACTGGGGTCGGACAGGGACTAATTCATGCCTCT

```
       GTTCCTCTATGACAATCTCATCGTCTTTTCACCTTCGGTAGAAGATTTTGGAGGAAATAT
361    ----------+----------+----------+----------+----------+----------+    420
       CAAGGAGATACTGTTAGAGTAGCAGAAAAGTGGAAGCCATCTTCTAAAACCTCCTTTATA

F  L  Y  D  N  L  I  V  F  S  P  S  V  E  D  F  G  G  N  I
                                                     _____

CAACGTGGAGACCATCAGTACCTTTATCGACGGCGGAGGCAGTGTCCTGGTAGCTGCCAG
421    ----------+----------+----------+----------+----------+----------+    480
       GTTGCACCTCTGGTAGTCATGGAAATAGCTGCCGCCTCCGTCACAGGACCATCGACGGTC

N  V  E  T  I  S  T  F  I  D  G  G  G  S  V  L  V  A  A  S
       _____

CTCAGACATCGGTGACCCTCTCCGCGAGCTGGGCAGTGAGTGTGGGATTGAGTTTGACGA
481    ----------+----------+----------+----------+----------+----------+    540
       GAGTCTGTAGCCACTGGGAGAGGCGCTCGACCCGTCACTCACACCCTAACTCAAACTGCT

*        *        *
        S  D  I  G  D  P  L  R  E  L  G  S  E  C  G  I  E  F  D  E

GGAGAAAACGGCCGTCATTGACCATCACAACTATGATGTCTCAGACCTCGGCCAGCACAC
541    ----------+----------+----------+----------+----------+----------+    600
       CCTCTTTTGCCGGCAGTAACTGGTAGTGTTGATACTACAGAGTCTGGAGCCGGTCGTGTG

*   *
        E  K  T  A  V  I  D  H  H  N  Y  D  V  S  D  L  G  Q  H  T

GCTCATTGTGGCCGACACTGAGAACCTGCTGAAGGCCCCGACCATCGTCGGGAAGTCATC
601    ----------+----------+----------+----------+----------+----------+    660
       CGAGTAACACCGGCTGTGACTCTTGGACGACTTCCGGGGCTGGTAGCAGCCCTTCAGTAG

```
         TCTGAATCCCATCCTCTTCCGAGGTGTTGGGATGGTGGCTGATCCTGACAATCCTTTGGT
     661 ---------+---------+---------+---------+---------+---------+ 720
         AGACTTAGGGTAGGAGAAGGCTCCACAACCCTACCACCGACTAGGACTGTTAGGAAACCA

L  N  P  I  L  F  R  G  V  G  M  V  A  D  P  D  N  P  L  V
          ―――――――――――――――――――――――――――――――

GCTGGACATCCTGACCGGCTCTTCTACCTCTTACTCCTTCTTCCCAGATAAACCCATCAC
     721 ---------+---------+---------+---------+---------+---------+ 780
         CGACCTGTAGGACTGGCCGAGAAGATGGAGAATGAGGAAGAAGGGTCTATTTGGGTAGTG

L  D  I  L  T  G  S  S  T  S  Y  S  F  F  P  D  K  P  I  T

GCAGTACCCGCACGCGGTGGGGAAGAACACGCTGCTCATCGCGGGGCTGCAGGCCCGGAA
     781 ---------+---------+---------+---------+---------+---------+ 840
         CGTCATGGGCGTGCGCCACCCCTTCTTGTGCGACGAGTAGCGCCCCGACGTCCGGGCCTT

Q  Y  P  H  A  V  G  K  N  T  L  L  I  A  G  L  Q  A  R  N

CAACGCCCGTGTCATCTTCAGCGGCTCCCTCGACTTCTTCAGCGATGCCTTCTTCAACTC
     841 ---------+---------+---------+---------+---------+---------+ 900
         GTTGCGGGCACAGTAGAAGTCGCCGAGGGAGCTGAAGAAGTCGCTACGGAAGAAGTTGAG

N  A  R  V  I  F  S  G  S  L  D  F  F  S  D  A  F  F  N  S
                ―――――――――――――――――――――――――――――――――――

CGCGGTGCAGAAGGCCACGCCTGGCTCCCAGAGGTATCCCCAGACAGGCAACTATGAGCT
     901 ---------+---------+---------+---------+---------+---------+ 960
         GCGCCACGTCTTCCGGTGCGGACCGAGGGTCTCCATAGGGGTCTGTCCGTTGATACTCGA

A  V  Q  K  A  T  P  G (S  Q  R) Y  P  Q  T  G  N  Y  E  L
          ―――

CGCCGTGGCCCTCTCCCGCTGGGTGTTCAAGGAGGAGGGTGTCCTCCGAGTGGGGCCTGT
     961 ---------+---------+---------+---------+---------+---------+ 1020
         GCGGCACCGGGAGAGGGCGACCCACAAGTTCCTCCTCCCACAGGAGGCTCACCCCGGACA

```
                GTCCCACCATCGGGTGGGCGAGAAAGCCCCACCCAACGCCTACACCGTCACTGACCTAGT
         1021   ------------+---------+---------+---------+---------+---------+  1080
                CAGGGTGGTAGCCCACCCGCTCTTTCGGGGTGGGTTGCGGATGTGGCAGTGACTGGATCA

S  H  H  R  V  G  E  K  A  P  P  N  A  Y  T  V  T  D  L  V

CGAGTACAGCATCGTGATTGAGCAGCTCTCACAGGGCAGATGGGTCCCCTTTGATGGCGA
         1081   ------------+---------+---------+---------+---------+---------+  1140
                GCTCATGTCGTAGCACTAACTCGTCGAGAGTGTCCCGTCTACCCAGGGGAAACTACCGCT

E  Y  S  I  V  I  E  Q  L  S  Q  G  R  W  V  P  F  D  G  D

CGACATTCAGCTGGAGTTTGTCCGCATCGATCCTTTCGTGAGGACCTTCTTGAAGAGGAA
         1141   ------------+---------+---------+---------+---------+---------+  1200
                GCTGTAAGTCGACCTCAAACAGGCGTAGCTAGGAAAGCACTCCTGGAAGAACTTCTCCTT

D  I  Q  L  E  F  V  R  I  D  P  F  V  R  T  F  L  K  R  K

AGGCGGCAAGTACAGCGTCCAGTTCAAGTTGCCGGACGTGTACGGCGTGTTCCAGTTCAA
         1201   ------------+---------+---------+---------+---------+---------+  1260
                TCCGCCGTTCATGTCGCAGGTCAAGTTCAACGGCCTGCACATGCCGCACAAGGTCAAGTT

G  G  K  Y  S  V  Q  F  K  L  P  D  V  Y  G  V  F  Q  F  K

AGTGGACTACAACCGGCTGGGCTACACGCACCTGTACTCCTCCACTCAGGTGTCCGTGCG
         1261   ------------+---------+---------+---------+---------+---------+  1320
                TCACCTGATGTTGGCCGACCCGATGTGCGTGGACATGAGGAGGTGAGTCCACAGGCACGC

V  D  Y  N  R  L  G  Y  T  H  L  Y  S  S  T  Q  V  S  V  R

GCCCCTGCAGGCACACGCAGTACGAGCGCTTCATCCCCTCGGCTTACCCCTACTACGCCA
         1321   ------------+---------+---------+---------+---------+---------+  1380
                CGGGGACGTCCGTGTGCGTCATGCTCGCGAAGTAGGGGAGCCGAATGGGGATGATGCGGT

```
       GCGCCTTCTCCATGATGGTCGGGCTCTTCATCTTCAGCGTCGTCTTCTTGCACATGAAGG
1381   ---------+---------+---------+---------+---------+---------+   1440
       CGCGGAAGAGGTACTACCAGCCCGAGAAGTAGAAGTCGCAGCAGAAGAACGTGTACTTCC

R  L  L  H  D  G  R  A  L  H  L  Q  R  R  L  L  A  H  E  G

AGAAGGAGAAGTCTGActgaggggccgggccgggcccccaggactccttacaacacacagg
1441   ---------+---------+---------+---------+---------+---------+   1500
       TCTTCCTCTTCAGACTgactccccggcccggcccggggtcctgaggaatgttgtgtgtcc

E  G  E  V  * gagggttttttataggcttgccttccccccccctttatggtgggctttgtttgttttttaaag
1501   ---------+---------+---------+---------+---------+---------+   1560
       ctcccaaaaatatccgaacggaaggggggggaaataccacccgaaacaaacaaaaatttc ccacggacaatggcacagcttacctcagtgggagatgcaagatgagtaccaggggtggt
1561   ---------+---------+---------+---------+---------+---------+   1620
       ggtgcctgttaccgtgtcgaatggagtcaccctctacgttctactcatggtcccccacca taggaataatttctaagttttttccaccttgaatgctgagtggtattttttcatatgtaaag
1621   ---------+---------+---------+---------+---------+---------+   1680
       atccttattaaagattcaaaaaggtggaacttacgactcaccataaaaagtatacatttc tcaactgatttctaaaataaaagaaaaacatcaccctcagaaaaaaaaaa
1681   ---------+---------+---------+---------+---------+            1730
       agttgactaaagattttatttctttttgtagtgggagtctttttttttt
```

FIG.3E

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
  ( A ) LENGTH: 1730 base pairs
  ( B ) TYPE: nucleic acid
  ( C ) STRANDEDNESS: single
  ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
  ( A ) ORGANISM: Pig ( i x ) FEATURE:
  ( A ) NAME/KEY: CDS
  ( B ) LOCATION: 140..1456

( x i ) SEQUENCE DESCRIPTION: SEQ ID NO:1:

```
AGCAGCTCCA TAGGCCCAGC CCCGGCGTAC AAGGATCACT TCCGGTGGTA CTTCACTACC        60

AAGAAGCTGC GATTGGGCGA GCGTGGAAGG GGCATTTCCG GTGTCCACCT GCTTGGGTTC       120

TTTGGACAGA AGTAGGAAG ATG GAG CTC GGC GCC GCG GCC CGT GCT TGG TCG       172
                    Met Glu Leu Gly Ala Ala Ala Arg Ala Trp Ser
                     1               5                      10

CTC TTG TGG CTG CTG CTT CCC TTG CTT GGC CTG GTC GGC GCC AGC GGT        220
Leu Leu Trp Leu Leu Leu Pro Leu Leu Gly Leu Val Gly Ala Ser Gly
            15                  20                  25

CCC CGT ACC TTA GTG CTT CTG GAC AAC CTC AAC CTG CGG GAG ACG CAT        268
Pro Arg Thr Leu Val Leu Leu Asp Asn Leu Asn Leu Arg Glu Thr His
        30                  35                  40

TCA CTT TTC TTC CGG AGC CTA AAG GAT CGG GGC TTC GTA CTC ACA TTC        316
Ser Leu Phe Phe Arg Ser Leu Lys Asp Arg Gly Phe Val Leu Thr Phe
    45                  50                  55

AAG ACC GCA GAT GAC CCC AGC CTG TCC CTG ATT AAG TAC GGA GAG TTC        364
Lys Thr Ala Asp Asp Pro Ser Leu Ser Leu Ile Lys Tyr Gly Glu Phe
60                  65                  70                  75

CTC TAT GAC AAT CTC ATC GTC TTT TCA CCT TCG GTA GAA GAT TTT GGA        412
Leu Tyr Asp Asn Leu Ile Val Phe Ser Pro Ser Val Glu Asp Phe Gly
                80                  85                  90

GGA AAT ATC AAC GTG GAG ACC ATC AGT ACC TTT ATC GAC GGC GGA GGC        460
Gly Asn Ile Asn Val Glu Thr Ile Ser Thr Phe Ile Asp Gly Gly Gly
            95                 100                 105

AGT GTC CTG GTA GCT GCC AGC TCA GAC ATC GGT GAC CCT CTC CGC GAG        508
Ser Val Leu Val Ala Ala Ser Ser Asp Ile Gly Asp Pro Leu Arg Glu
        110                 115                 120

CTG GGC AGT GAG TGT GGG ATT GAG TTT GAC GAG GAG AAA ACG GCC GTC        556
Leu Gly Ser Glu Cys Gly Ile Glu Phe Asp Glu Glu Lys Thr Ala Val
    125                 130                 135

ATT GAC CAT CAC AAC TAT GAT GTC TCA GAC CTC GGC CAG CAC ACG CTC        604
Ile Asp His His Asn Tyr Asp Val Ser Asp Leu Gly Gln His Thr Leu
140                 145                 150                 155

ATT GTG GCC GAC ACT GAG AAC CTG CTG AAG GCC CCG ACC ATC GTC GGG        652
Ile Val Ala Asp Thr Glu Asn Leu Leu Lys Ala Pro Thr Ile Val Gly
                160                 165                 170
```

```
AAG TCA TCT CTG AAT CCC ATC CTC TTC CGA GGT GTT GGG ATG GTG GCT      700
Lys Ser Ser Leu Asn Pro Ile Leu Phe Arg Gly Val Gly Met Val Ala
        175                 180                 185

GAT CCT GAC AAT CCT TTG GTG CTG GAC ATC CTG ACC GGC TCT TCT ACC      748
Asp Pro Asp Asn Pro Leu Val Leu Asp Ile Leu Thr Gly Ser Ser Thr
            190                 195                 200

TCT TAC TCC TTC TTC CCA GAT AAA CCC ATC ACG CAG TAC CCG CAC GCG      796
Ser Tyr Ser Phe Phe Pro Asp Lys Pro Ile Thr Gln Tyr Pro His Ala
205                 210                 215

GTG GGG AAG AAC ACG CTG CTC ATC GCG GGG CTG CAG GCC CGG AAC AAC      844
Val Gly Lys Asn Thr Leu Leu Ile Ala Gly Leu Gln Ala Arg Asn Asn
220                 225                 230                 235

GCC CGT GTC ATC TTC AGC GGC TCC CTC GAC TTC TTC AGC GAT GCC TTC      892
Ala Arg Val Ile Phe Ser Gly Ser Leu Asp Phe Phe Ser Asp Ala Phe
                240                 245                 250

TTC AAC TCC GCG GTG CAG AAG GCC ACG CCT GGC TCC CAG AGG TAT CCC      940
Phe Asn Ser Ala Val Gln Lys Ala Thr Pro Gly Ser Gln Arg Tyr Pro
            255                 260                 265

CAG ACA GGC AAC TAT GAG CTC GCC GTG GCC CTC TCC CGC TGG GTG TTC      988
Gln Thr Gly Asn Tyr Glu Leu Ala Val Ala Leu Ser Arg Trp Val Phe
            270                 275                 280

AAG GAG GAG GGT GTC CTC CGA GTG GGG CCT GTG TCC CAC CAT CGG GTG     1036
Lys Glu Glu Gly Val Leu Arg Val Gly Pro Val Ser His His Arg Val
285                 290                 295

GGC GAG AAA GCC CCA CCC AAC GCC TAC ACC GTC ACT GAC CTA GTC GAG     1084
Gly Glu Lys Ala Pro Pro Asn Ala Tyr Thr Val Thr Asp Leu Val Glu
300                 305                 310                 315

TAC AGC ATC GTG ATT GAG CAG CTC TCA CAG GGC AGA TGG GTC CCC TTT     1132
Tyr Ser Ile Val Ile Glu Gln Leu Ser Gln Gly Arg Trp Val Pro Phe
                320                 325                 330

GAT GGC GAC GAC ATT CAG CTG GAG TTT GTC CGC ATC GAT CCT TTC GTG     1180
Asp Gly Asp Asp Ile Gln Leu Glu Phe Val Arg Ile Asp Pro Phe Val
                335                 340                 345

AGG ACC TTC TTG AAG AGG AAA GGC GGC AAG TAC AGC GTC CAG TTC AAG     1228
Arg Thr Phe Leu Lys Arg Lys Gly Gly Lys Tyr Ser Val Gln Phe Lys
            350                 355                 360

TTG CCG GAC GTG TAC GGC GTG TTC CAG TTC AAA GTG GAC TAC AAC CGG     1276
Leu Pro Asp Val Tyr Gly Val Phe Gln Phe Lys Val Asp Tyr Asn Arg
365                 370                 375

CTG GGC TAC ACG CAC CTG TAC TCC TCC ACT CAG GTG TCC GTG CGG CCC     1324
Leu Gly Tyr Thr His Leu Tyr Ser Ser Thr Gln Val Ser Val Arg Pro
380                 385                 390                 395

CTG CAG GCA CAC GCA GTA CGA GCG CTT CAT CCC CTC GGC TTA CCC CTA     1372
Leu Gln Ala His Ala Val Arg Ala Leu His Pro Leu Gly Leu Pro Leu
                400                 405                 410

CTA CGC CAG CGC CTT CTC CAT GAT GGT CGG GCT CTT CAT CTT CAG CGT     1420
Leu Arg Gln Arg Leu Leu His Asp Gly Arg Ala Leu His Leu Gln Arg
            415                 420                 425

CGT CTT CTT GCA CAT GAA GGA GAA GGA GAA GTC TGACTGAGGG GCCGGGCGG    1473
Arg Leu Leu Ala His Glu Gly Glu Gly Glu Val
            430                 435

GCCCCAGGAC TCCTTACAAC ACACAGGGAG GGTTTTATA GGCTTGCCTT CCCCCCCCTT    1533

TATGGTGGGC TTTGTTTGTT TTTAAAGCCA CGGACAATGG CACAGCTTAC CTCAGTGGGA   1593

GATGCAAGAT GAGTACCAGG GGGTGGTTAG GAATAATTTC TAAGTTTTTC CACCTTGAAT   1653

GCTGAGTGGT ATTTTTCATA TGTAAAGTCA ACTGATTTCT AAAATAAAAG AAAAACATCA   1713

CCCTCAGAAA AAAAAAA                                                  1730
```

( 2 ) INFORMATION FOR SEQ ID NO:2:

(i) SEQUENCE CHARACTERISTICS:
 (A) LENGTH: 438 amino acids
 (B) TYPE: amino acid
 (D) TOPOLOGY: linear (ii) MOLECULE TYPE: protein (xi) SEQUENCE DESCRIPTION: SEQ ID NO:2:

```
Met Glu Leu Gly Ala Ala Ala Arg Ala Trp Ser Leu Leu Trp Leu Leu
 1               5                  10                  15

Leu Pro Leu Leu Gly Leu Val Gly Ala Ser Gly Pro Arg Thr Leu Val
             20                  25                  30

Leu Leu Asp Asn Leu Asn Leu Arg Glu Thr His Ser Leu Phe Phe Arg
         35                  40                  45

Ser Leu Lys Asp Arg Gly Phe Val Leu Thr Phe Lys Thr Ala Asp Asp
     50                  55                  60

Pro Ser Leu Ser Leu Ile Lys Tyr Gly Glu Phe Leu Tyr Asp Asn Leu
 65                  70                  75                  80

Ile Val Phe Ser Pro Ser Val Glu Asp Phe Gly Gly Asn Ile Asn Val
                 85                  90                  95

Glu Thr Ile Ser Thr Phe Ile Asp Gly Gly Gly Ser Val Leu Val Ala
                100                 105                 110

Ala Ser Ser Asp Ile Gly Asp Pro Leu Arg Glu Leu Gly Ser Glu Cys
             115                 120                 125

Gly Ile Glu Phe Asp Glu Glu Lys Thr Ala Val Ile Asp His His Asn
     130                 135                 140

Tyr Asp Val Ser Asp Leu Gly Gln His Thr Leu Ile Val Ala Asp Thr
145                 150                 155                 160

Glu Asn Leu Leu Lys Ala Pro Thr Ile Val Gly Lys Ser Ser Leu Asn
                165                 170                 175

Pro Ile Leu Phe Arg Gly Val Gly Met Val Ala Asp Pro Asp Asn Pro
                180                 185                 190

Leu Val Leu Asp Ile Leu Thr Gly Ser Ser Thr Ser Tyr Ser Phe Phe
             195                 200                 205

Pro Asp Lys Pro Ile Thr Gln Tyr Pro His Ala Val Gly Lys Asn Thr
    210                 215                 220

Leu Leu Ile Ala Gly Leu Gln Ala Arg Asn Asn Ala Arg Val Ile Phe
225                 230                 235                 240

Ser Gly Ser Leu Asp Phe Phe Ser Asp Ala Phe Phe Asn Ser Ala Val
                245                 250                 255

Gln Lys Ala Thr Pro Gly Ser Gln Arg Tyr Pro Gln Thr Gly Asn Tyr
            260                 265                 270

Glu Leu Ala Val Ala Leu Ser Arg Trp Val Phe Lys Glu Glu Gly Val
        275                 280                 285

Leu Arg Val Gly Pro Val Ser His His Arg Val Gly Glu Lys Ala Pro
    290                 295                 300

Pro Asn Ala Tyr Thr Val Thr Asp Leu Val Glu Tyr Ser Ile Val Ile
305                 310                 315                 320

Glu Gln Leu Ser Gln Gly Arg Trp Val Pro Phe Asp Gly Asp Asp Ile
                325                 330                 335

Gln Leu Glu Phe Val Arg Ile Asp Pro Phe Val Arg Thr Phe Leu Lys
            340                 345                 350

Arg Lys Gly Gly Lys Tyr Ser Val Gln Phe Lys Leu Pro Asp Val Tyr
        355                 360                 365

Gly Val Phe Gln Phe Lys Val Asp Tyr Asn Arg Leu Gly Tyr Thr His
```

-continued

| | | | | | | | | | | | | | | | |
|---|---|---|---|---|---|---|---|---|---|---|---|---|---|---|---|
| | 370 | | | | | 375 | | | | | 380 | | | | |
| Leu | Tyr | Ser | Ser | Thr | Gln | Val | Ser | Val | Arg | Pro | Leu | Gln | Ala | His | Ala |
| 385 | | | | | 390 | | | | | 395 | | | | | 400 |
| Val | Arg | Ala | Leu | His | Pro | Leu | Gly | Leu | Pro | Leu | Leu | Arg | Gln | Arg | Leu |
| | | | | 405 | | | | | 410 | | | | | 415 | |
| Leu | His | Asp | Gly | Arg | Ala | Leu | His | Leu | Gln | Arg | Arg | Leu | Leu | Ala | His |
| | | | 420 | | | | | 425 | | | | | 430 | | |
| Glu | Gly | Glu | Gly | Glu | Val | | | | | | | | | | |
| | | 435 | | | | | | | | | | | | | |

BINDING ASSAY UTILIZING A NUCLEIC ACID ENCODING APAMIN BINDING PROTEIN

This application is a division of co-pending application Ser. No. 08/314,979 filed Sep. 29, 1994, which is a Continuation application of U.S. Ser. No. 07/923,095, filed Jul. 30, 1992, now U.S. Pat. No. 5,401,652.

Potassium (K) channels are integral membrane proteins of great molecular and functional diversity, present in practically all mammalian cells. These channels are primarily responsible for maintaining a resting membrane potential and are rapidly activated in response to an external depolarizing stimulus, binding of certain ligands, or changes in the intracellular concentration of calcium or ATP. In the excitable cells such as neurons or cardiac myocytes, K-channels determine the duration of the action potential thus performing a vital function in the CNS and the cardiac functions (reviewed in 1–2) The calcium-activated K-channel sub-family consists of at least three discernible ionic currents; a large ("BK"), an intermediate ("IK") and a small conductance ("SK") channels (Reviewed in 3–5). These K-channels are activated in response to a rise in the intracellular concentration of calcium [$Ca^{2+}$]i. In addition to [$Ca^{2+}$]i, the "BK" and "IK" channels are also sensitive to the changes in the membrane potential, whereas "SK" channel has no significant voltage sensitivity.

Functionally, the SK-channel is involved in the afterhyperpolarization that follows action potentials in many neurons. These include the sympathetic ganglionic neurons, hippocampal neurons, neurosecretory neurons and spinal motoneurons, as well as the skeletal muscle cells (1, 5–9). Furthermore, the SK-channel has been suggested to play a major role in the spontaneous transient outward currents in the tracheal smooth muscle cells (10), the inhibitory action of the $\alpha_1$-adrenoceptors, neurotensin receptor and the $P_2$-subtype of the ATP receptor (4, 9).

The neuronal and the skeletal muscle SK-channel is specifically and avidly blocked by a bee venom-derived peptide toxin, apamin (5, 11–14). By all indications, the apamin receptor complex is either identical to, or closely associated with the SK-channel. Apamin is an 18 amino acid neurotoxic peptide which has a single class of binding sites in the rat brain synaptosomes and brain slices with an apparent dissociation constant ($K_d$) of 10–25 pM (15, 16). Apamin is also capable of a temperature dependent and high affinity ($K_d$=30–150 pM) binding to the detergent solubilized brain receptor sites (17–20). The reported $B_{max}$ value for the rat brain synaptosomes and brain slices is 10–30 fmol/mg protein (16, 17, 20), while that for the detergent solubilized receptor ranges from 0.45 to 17 fmol/mg protein (18, 19).

The polypeptide components of the apamin receptor have been studied by several groups. Cross-linking experiments using [$^{125}$I] apamin, followed by SDS-PAGE and autoradiography have indicated that the apamin binding proteins of the rat brain synaptosomal membrane consist of two protein species, a major 80–86 KDa protein and, in most reported preparations, a minor 50–59 KDa band (17, 21, 22). Partial peptide mapping of the two protein bands, using an anti-apamin anti-serum, has shown that the smaller polypeptide is likely to be a proteolytic fragment of the larger protein and not an additional subunit of the apamin binding protein in the brain. Furthermore, in the plasma membrane of the cultured neurons or astrocytes, there are additional components with the ability to cross-link to [$^{125}$I]apamin. Cross-linking of [$^{125}$I]apamin to the membranes from the rat heart, liver and smooth muscle has also indicated that a 85–87 KDa polypeptide is the major labeled component of the apamin binding complex (23). A second 59 KDa protein was identified in the liver membrane only (23).

The blocking of the small conductance calcium activated potassium channel (sKca) results in prolongation of the action potential, while its activation by an increase in the intracellular calcium concentration accelerates the rate of hyperpolarization, thus shortening the duration of the action potential. In vascular smooth muscle cells (such as those in veins and arteries), activation of sKca results in the hyperpolarization of the smooth muscle membrane, which in turn results in the inhibition of the voltage-gated calcium channels. The inhibition of the latter may then lead to the relaxation of the blood vessels and lowering of the blood pressure. In the heart, modulation of sKca can be a potentially useful means to regulate an arrhythmic heart. In the nervous system, the hippocampus of Alzheimer's patients shows a drastic reduction in apamin denisty (30). Further apamin receptor in neurons has been reported to be involved in the process of learning and memory (42). Thus, manipulation of this receptor may also result in improving cognition. Notwithstanding the significant therapeutic potential manipulation of sKca may have, relatively little is known about the identity of the proteins involved in this channel. The present invention now provides a key element in the study of the potassium channel function.

SUMMARY OF THE INVENTION

The present invention relates to a nucleic acid fragment comprising a sequence encoding an apamin receptor, as well as the recombinantly produced apamin receptor per se. Such receptors are associated with calcium activated potassium channels in a variety of animal tissues, such as brain, skeletal, cardiac, vascular smooth muscle, pancreas, kidney and liver tissue. An exemplary sequence of Kcal 1.8, a porcine receptor, is provided in FIGS. 3A–3E; however, the invention also encompasses any nucleotide sequence which hybridizes, under medium or high stringency conditions (as defined in the Examples below), with a nucleotide sequence encoding the amino acid sequence of FIGS. 3A–3E as well as the biologically active proteins and fragments encoded by such sequences. By "biologically active" is meant proteins or fragments which are capable of eliciting production of antibodies capable of binding to the receptor, as well as proteins or fragments which are associated with calcium activated K+ channels (such as "BK" or "IK") but do not necessarily bind apamin.

The invention also relates to host cells and recombinant vectors useful in expressing the apamin receptor gene and protein. Such hosts will provide a convenient basis for development of screens designed to identify compounds which are capable of modulating activity of the receptor and thus, modulate the activity of the potassium channel. In the heart, modulation of this channel provides a means for regulating an arrhythmic heart; thus, any drug that can open or close this potassium channel is considered a potential antiarrhythmic agent. Similarly, in vascular smooth muscle cells, such as those in veins and arteries, activation of the potassium channel results in hyperpolarization of the smooth muscle membrane, which in turn results in the inhibition of the voltage-gated calcium channels. The inhibition of the latter will then lead to relaxation of the blood vessels and lowering of blood pressure. The receptor is also associated with cognition functions. As noted above, receptor density decreases in Alzheimer's patients, and is involved in the process of learning and memory. Thus, compounds which activate the receptor may be useful in improving impaired cognitive function in Alzheimer's patients, or to enhance memory and learning capacity. Therefore, a convenient system enabling the detection of compounds that modulate potassium channel activity has the potential for identifying drugs with tremendous therapeutic utility. Also, the isolated nucleic acid sequence detectably labelled can be used as a diagnostic probe for Alzheimer's disease, by determining the level of expression of such receptors in peripheral neurons of individuals suspected of being affected. Copending and cofiled applications which have as common inventors Mohammod Rena Zial and Patricia Tyson Sofol, relating to purified apamin binding proteins [Ser. No. 07/922, 307], and affinity matrix for binding protein purification [Ser. No. 07/922,604], are each incorporated herein by reference in their entirety.

BRIEF DESCRIPTION OF THE FIGURES

FIG. 1: Northern blotting of the mRNA encoding the apamin receptor.

FIG. (1A) Poly A$^+$-mRNA isolated from adult rat brain (lane 1), or bovine brain (lane 2) or porcine brain (lane 3) are separated on a denaturing agarose gel, blotted onto nitrocellulose, hybridized with $^{32}$P-labelled Kcal 1.6 cDNA and autoradiographed.

FIG. (1B) Poly A$^+$-mRNA isolated from the neonatal rat brain are separated on a denaturing agarose gel, blotted onto nitrocellulose, hybridized with $^{32}$p-labelled Kcal 1.6 cDNA and autoradiographed. The arrows indicate the size (in kilobases) of the two hybridized mRNA bands.

Figure 2:
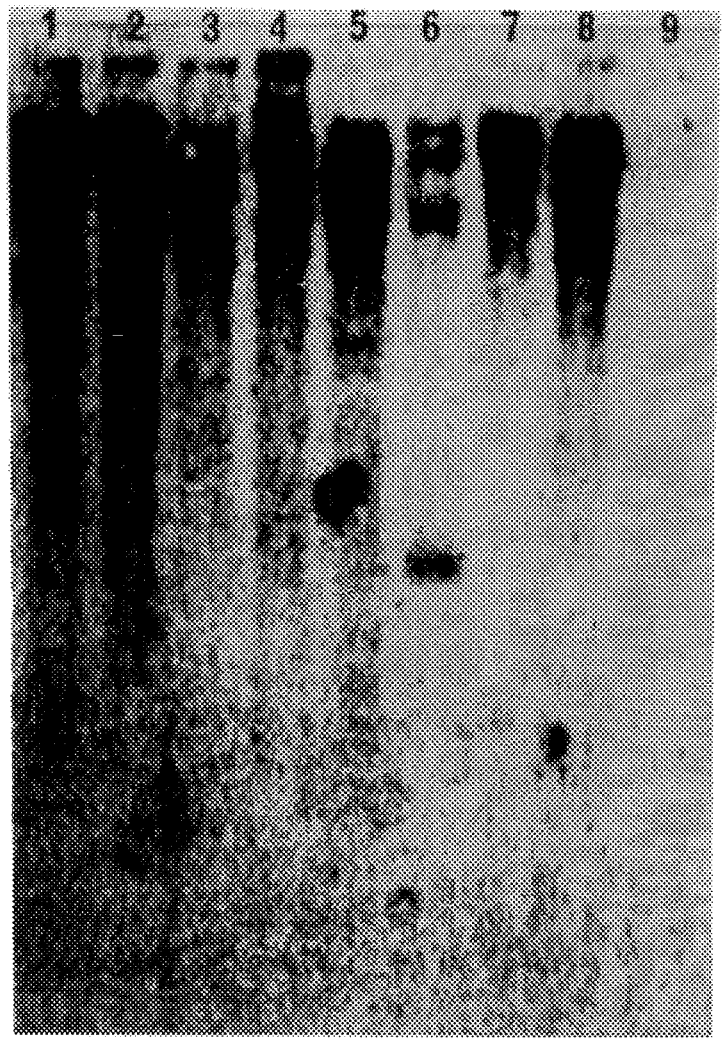

FIG. 2: Genomic Southern hybridization analysis of Kcal 1.6. EcoRI cut-genomic DNA from human (lane 1), monkey (lane 2), rat (lane 3), mouse (lane 4), dog (lane 5), cow (lane 6), rabbit (lane 7), chicken (lane 8) and yeast (lane 9) are hybridized with $^{32}$p-labelled Kcal 1.6 cDNA and autoradiographed.

FIGS. 3A–3E: The nucleotide sequence (SEQ ID NO. 1) and its amino acid translation (SEQ ID NO: 2) of Kcal-1.8 cDNA. The underlined amino acids indicate the potential transmembrane domains of the protein, The oval represents the potential site for protein kinase C. The (*) indicate amino acids which form a potential calcium binding site.

Figure 4:
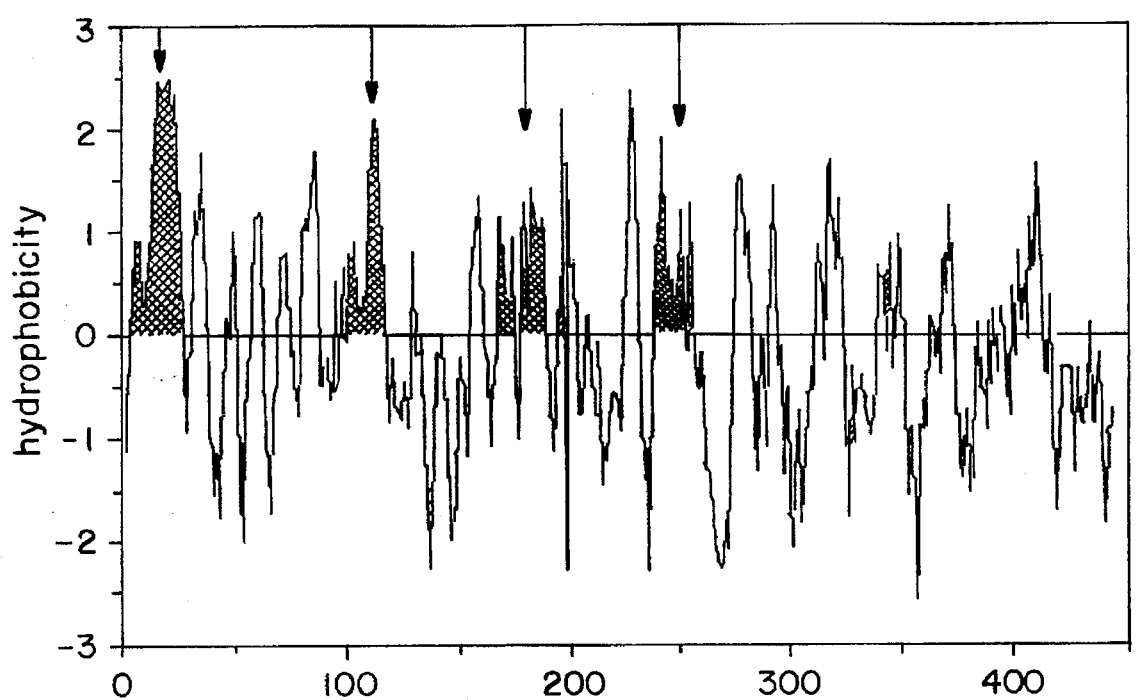

FIG. 4: The hydropathy plot for the protein encoded by Kcal-1.8 cDNA. The four putative but strong hydrophobic domains are indicated by arrows.

Figure 5:
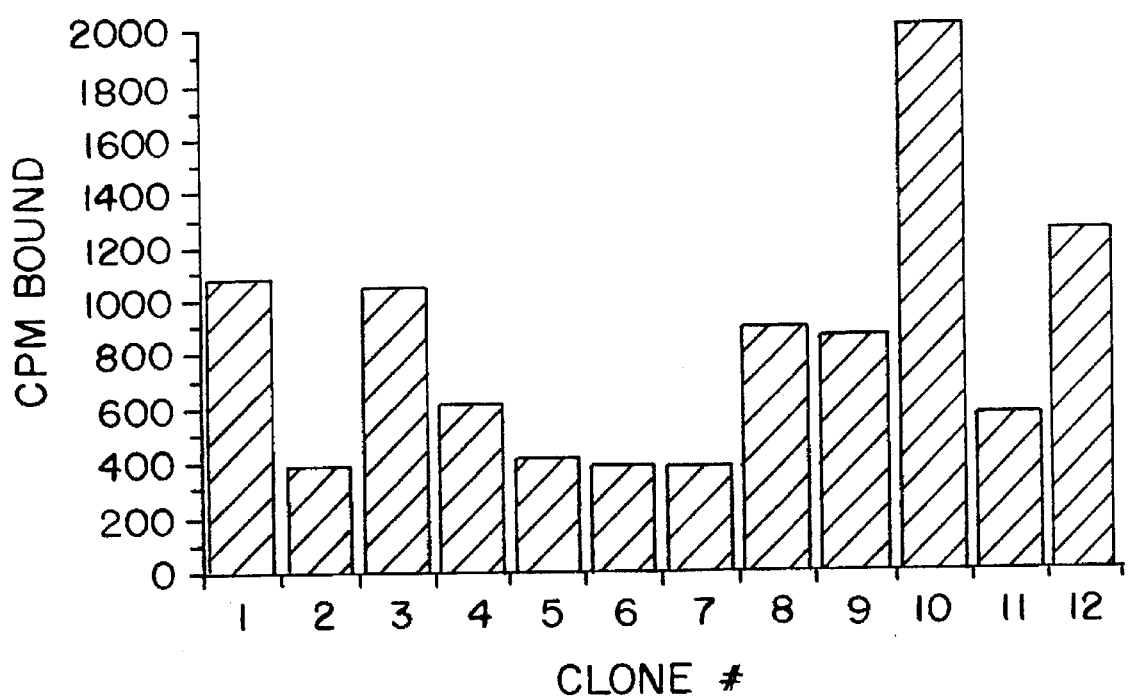

FIG. 5: Binding of apamin to plasma membrane of CV-1 cells transfected with Kcal-1.8 cDNA in a pRC/CMV vector.

DETAILED DESCRIPTION OF THE VECTOR

A full-length apamin binding protein nucleic acid sequence, presumed to be associated with a calcium activated K$^+$ channel, is first isolated from a porcine vascular smooth muscle (aorta) expression cDNA library in a λ-ZAP vector. The library is screened with polyclonal sera raised against a bovine brain apamin receptor. Screening of about 2 million plaque forming units yields four positive plaques which are rescreened and plaque purified.

The λ-ZAP is transformed into "pBluescript" plasmid by standard techniques, the DNA is digested with the restriction endonucleases EcoRI and XhoI to release the cDNA inserts and analyzed by agarose gel electrophoresis. One 1.6 Kb cDNA clone (designated Kcal 1.6) is selected for Northern hybridization, genomic Southern blotting and DNA sequencing. As shown in FIG. 1A, the cDNA Kcal 1.6 detects a single mRNA band of approximately 2.1 Kb in the adult rat brain mRNA (lane 1), bovine brain mRNA (lane 2) and porcine brain mRNA (lane 3). The probe, however, reveals two mRNA bands of 2.1 and 3.0 Kb in size in the Northern blot of mRNA from neonatal rat brain (FIG. 1B). These results suggest that in the neonatal rat brain, there are two distinct mRNA species which hybridize to Kcal 1.6, possibly arising by the alternate splicing of mRNA.

Next, an EcoRI cut-genomic Southern blot is probed with Kcal 1.6 cDNA. As shown in FIG. 2, after repeated washing of the blot at high stringency, the Kcal 1.6 probe detects a single 14 Kb band in human (lane 1) and in monkey (lane 2). However, there are variable patterns of hybridization in the rat (lane 3), mouse (lane 4), canine (lane 5), bovine (lane 6), rabbit (lane 7) and chicken (lane 8). There is no detectable hybridization with the yeast DNA (lane 9). This experiment indicates that there are significant sequence homologies among the genes encoding p80 in various species. Furthermore, the gone(s) encoding p80 in human and monkey are probably more similar than those in other species.

Kcal 1.6 cDNA is then sequenced. The nucleotide sequence obtained indicates that the clone is not of full length and lacks the initiation methionine residue. To obtain a full-length clone, Kcal 1.6 is used as a probe and the original porcine aorta cDNA library is screened, and positive clones analyzed by restriction mapping and electrophoresis for relatedness and insert size. One cDNA clone (designated Kcal 1.8), which appears to be slightly longer than Kcal 1.6, is selected and sequenced by a Taq polymerase sequencing technique. When the nucleotide sequence is translated in frame, the cDNA Kcal 1.8 encodes a protein of 437 amino acids (FIG. 3A–3E), with an initiation methionine and a stop site. Hydrophobicity analysis (FIG. 4) of the sequence indicates the presence of four strongly hydrophobic putative transmembrane domains (TMD1–4), a short amino terminus and a long carboxyl terminus. The sequence has some interesting features. It contains a strong "EF-Hand" consensus sequence (in FIG. 3B, indicated by a *). The EF-Hand consensus sequence is present in virtually all calcium binding protein members of calmodulin and troponin C families. In fact, the EF-Hand motif in Kcal 1.8 almost perfectly matches that of calmodulin, as well as a recently cloned component of Drosophila calcium activated K-channel, "Slo" (28). In addition, the sequence flanking the putative "EF-Hand" motif of Kcal 1.8 has significant homology with a number of known calcium binding proteins including troponin C, myosin, calreticulin, PEP-19, and several others. Since the small conductance calcium-activated potassium channel (skca) must have a calcium binding site, it gives further support to the belief that Kcal 1.8 indeed encodes skca. If the "EF-Hand" motif is in fact a calcium binding site of Kcal 1.8 protein, it places the "EF-Hand" motif on the cytoplasmic side of the membrane. The amino acid sequence of Kcal 1.8 also contains one protein kinase C site, and one tyrosine kinase phosphorylation site (not shown). In addition, a "leucine zipper" motif can be identified in the C-terminal portion of the protein (FIG. 3E, boxed "L"). At present, the significance, if any, of this motif in Kcal 1.8 is unclear. However, the presence of these putative phosphorylation sites, together with the "EF-Hand" motif are likely to place both N- and C-termini of the protein in the cytoplasmic side of the plasma membrane.

To further confirm Kcal 1.8's identity as an apamin receptor, Kcal cDNA is introduced into a stable mammalian expression vector, pRC/CMV, which is used to transfect CV-1 cells (African green monkey kidney). Cells stably expressing the Kcal 1.8 gene product are selected and are contacted with radiolabelled apamin, in the presence or absence of unlabelled apamin. A number of transfectants show enhanced binding of radio-labelled apamin, thereby adding further confirmation of Kcal 1.8's identity.

The foregoing discussion, and the sequences provided in FIGS. 3A–3E, relate to a porcine smooth muscle apamin receptor. However, it will be understood that the invention encompasses more than the specific exemplary sequences. Modifications to the sequence, such as deletions, insertions, or substitutions in the sequence which produce silent changes in the resulting protein molecule are also contemplated. For example, alteration in the gene sequence which reflect the degeneracy of the genetic code, or which result in the production of a chemically equivalent amino acid at a given site, are contemplated; thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a biologically equivalent product. Nucleotide changes which result in alteration of the N-terminal and C-terminal portions of the protein molecule would also not be expected to alter the activity of the protein. It may also be desirable to eliminate one or more of the cysteines present in the sequence, as the presence of cysteines may result in the undesirable formation of multimers when the protein is produced recombinantly, thereby complicating the purification and crystallization processes. In some cases, it may in fact be desirable to make mutants of the sequence in order to study the effect of alteration on the biological activity of the protein. Each of the proposed modifications is well within the routine skill in the art, as is determination of retention of biological activity of the encoded products.

The invention also encompasses homologous sequences obtained from other species and other tissues. As has already been demonstrated above, the nucleic acid sequence depicted in FIGS. 3A–3E hybridizes, under relatively stringent conditions, with nucleic acid fragments present in a number of other species, including human, thus demonstrating the ability to isolate other non-porcine sequences. Moreover, apamin receptors from tissue types other than vascular smooth muscle are also known to exist. Brain, skeletal muscle, and liver, in addition to vascular smooth muscle, have been repeatedly demonstrated to express a single class of binding site (4, 15–20). On the other hand, cardiac tissue seems to exhibit a heterogeneous population of target sites. The sequence disclosed in FIGS. 3A–3E can thus be used as a probe to isolate the corresponding receptors from other species and tissues. Alternate receptor types are isolatable as follows. cDNA libraries prepared from mRNA from the specific tissue type of interest are probed with radiolabelled Kcal 1.8 cDNA and washed under medium stringency (e.g., 1×SSC, 0.1% SDS, 55° C.). Plaques which appear positive are rescreened to verify authenticity. The positive plaques are then used in plasmid rescue according to techniques known in the art. Rescued plasmids are purified, cut with appropriate restriction enzymes, and analyzed in an agarose gel stained with ethidium bromide. The second gel is transferred to an nitrocellulose filter, probed with labelled Kcal 1.8, washed sequentially under a medium, then high stringency (0.1×SSC, 0.1% SDS, at 65° C.) wash and exposed to X-ray film. Those inserts which strongly hybridize to Kcal 1.8 under high stringency conditions represent likely receptor cDNA candidates. Further confirmation of the identity of these putative receptors can be accomplished according to the protocols described in the following examples, or in accordance with routine techniques known in the art. Thus, the invention encompasses not only the nucleotide and amino acid sequences depicted in FIGS. 3A–3E, but also nucleotide sequences which hybridize, under medium or high stringency conditions, with nucleotide sequence encoding the amino acid sequence of FIGS. 3A–3E, as well as the biologically active proteins or fragments encoded thereby.

The nucleic acid sequence can be used to express the receptor protein in a variety of host cells, both prokaryotic and eukaryotic for the chosen cell line. Examples of suitable eukaryotic cells include mammalian cells, plant cells, yeast cells, and insect cells. Suitable prokaryotic hosts include *Escherichia coli* and *Bacillus subtills*.

Suitable expression vectors are selected based upon the choice of host cell. Numerous vectors suitable for use in transforming bacterial cells are well known. For example, plasmids and bacteriophages, such as λ phage, are the most commonly used vectors for bacterial hosts, and for *E. coli* in particular. In both mammalian and insect cells, virus vectors are frequently used to obtain expression of exogenous DNA. In particular, mammalian cells are commonly transformed with SV40, polyoma virus, or transfected with plasmids such as pRC/CMV; and insect cells in culture may be transformed with baculovirus expression vectors. Yeast vector systems include yeast centromere plasmids, yeast episomal plasmids and yeast integrating plasmids. The invention encompasses any and all host cells transformed or transfected by the claimed nucleic acid fragments, as well as expression vectors used to achieve this. In particular, the host cells chosen for transfection are cells which exhibit only low (i.e., background) levels of receptor expression (e.g., see FIG. 5) before transcription.

In a preferred embodiment, nucleic acid sequences encoding an apamin receptor are used to transfect eukaryotic cells, preferably mammalian cells. For an initial determination of the ability of a given sequence to produce an apamin binding protein, transient expression, using plasmids such as pcDNAI or PSG5 into which the putative receptor DNA sequence has been ligated, and CMT-1 or COS-1 or -7 cells, can be employed. CMT-1 cells are transfected using the calcium phosphate precipitation method, and within 24 hours of transfection, the SV40 large T antigen is induced with addition of zinc to the medium. Seventy-two hours after transfection, cells are harvested for either RNA isolation or apamin binding assays. Expression is compared between cDNA and mock-transfected cells to determine if receptor activity is achieved by transfected cells. A positive host cell is preferably one which exhibits about twice the background level of apamin binding observed in non-transfected host cells of the same type.

For use of the sequences in screen development, stable expression of the DNA may be desirable. In this case, the DNA encoding the receptor is ligated into a stable vector containing a selectable marker, such as pRC/CMV, pcDNAI Neo, pXTI, or pMAM Neo. The plasmid DNA is linearized and introduced into an appropriate cell line for such vectors, e.g., CV-1, CHO, HepG-2 or NIH3T3 cells, by electroporation. Successfully transfected cells are identified by selection and isolated clones are picked and amplified. To determine transcription of Kcal message, cellular RNA is isolated and separated electrophoretically on agarose gel. Detection of endogenous and exogenous mRNA is accomplished using Kcal 1.8 as a probe.

Identification of exogenous (transfected) mRNA is accomplished by probing with a 400 bp fragment from the 5' untranslated region of cDNA, since this region is most divergent among species, diminishing the incidence of cross-hybridization.

The ability of any given isolated DNA sequence to yield a functional apamin receptor is determinable by a simple apamin binding assay. Transfected cells are prepared as previously described (41). Binding assays are performed by a standard procedure (16), and values for maximum binding of ligand to receptor (Bmax) and dissociation constant (Kd) for each cell line is calculated.

Further evaluation of the measurement of potassium channel activity in cultured transfectant cells is accomplished by $^{86}$Rb efflux assay (30, incorporated herein by reference). Briefly, stably transfected cells are loaded overnight with $^{86}$Rb in microtiter plates; the medium is then discarded and adherent cells washed three times to remove isotope. Cells are then incubated for 30 minutes at 37° C. with an isotonic buffer containing 20 mM $CaCl_2$ and 100 µM calcium ionophore A23187. The supernatants from wells are recovered and counted. The cell layer is solubilized in Triton X-100 and also counted, and the percent efflux of $^{86}$Rb calculated as described. The experiment is carried out in the presence or absence of 1 mM apamin (an sKca blocker) or 1 µM charybdotoxin (a BKca blocker), and control experiments carried out in parallel with cells being incubated with buffer, but without added ionophore. The percent efflux in transfectants harboring cloned DNA mock transfectants, and wild-type CV-1 cells (to measure endogenous efflux) are compared. Such assays are also useful in determining the effect of structural change in the channel in its function, and also to evaluate functional differences between different receptor subtypes. This assay is useful both in confirming activity of a putative receptor/channel as well as confirming the effects.

DEPOSIT OF BIOLOGICAL MATERIALS

The following biological materials were deposited with the American Type Culture Collection, 12301 Parklawn Drive, Rockville, Maryland, on June 1992, and given the Accession Numbers indicated:

| Material | Accession No. |
|---|---|
| E. coli containing pBluescript plasmid containing Kcal 1.8 | ATCC 69017 |

The present invention is further illustrated by the following non-limiting examples.

EXAMPLES

1. Screening Expression Library

A porcine aorta expression cDNA library in λ-Uni ZAP λR (Stratagens, La Jolla, Calif.) is probed with a 1:1000 dilution of a murine anti-apamin binding protein polyclonal antiserum (M2) using the Vectastain ABC kit (Vector Laboratories Inc., Burlingame, Calif.) as the secondary antibody and detection system. Approximately $2 \times 10^6$ plaque forming units are screened in this manner.

Four positive plaques are selected from the first round of screening. These are subjected to a re-screen and plasmids (pBluescript) containing the cDNA inserts are rescued using a helper phage. The parent plasmid DNA is digested with the restriction endonucleases EcoRI and XhoI to release the cDNA inserts and analyzed by agarose gel electrophoresis. One 1.6 Kb cDNA clone (designated Kcal 1.6) is selected for Northern hybridization, genomic Southern blotting and DNA sequencing. For Northern hybridization, polyA mRNA is isolated from frozen rat tissues using "Fast Track" mRNA isolation kit (Invitrogen, San Diego, Calif.) or purchased from Clontech Labs (Palo Alto, Calif.). Genomic Southern blot, "Zoo-blot" is purchased from Clontech Labs and processed as described by the manufacturer. As shown in FIG. 1A, the cDNA Kcal 1.6 detects a single mRNA band of approximately 2.1 Kb in the adult rat brain mRNA (lane 1) bovine brain mRNA (lane 2) and porcine brain mRNA (lane 3). The probe, however, reveals two mRNA bands of 2.1 and 3.0 Kb in size in the northern blot of mRNA from neonatal rat brain (FIG. 1B). These results may indicate that in the neonatal rat brain, there are two distinct mRNA species which hybridize to Kcal 1.6, possibly arising from the alternate splicing of mRNA. Next, an EcoRI cut-genomic southern blot is probed with Kcal 1.6 cDNA. As shown in FIG. 2, after repeated washing of the blot at high stringency, the Kcal 1.6 probe detects a single 14 Kb band in human (lane 1) and in monkey (lane 2). However, there are variable patterns of hybridization in the rat (lane 3), mouse (lane 4), canine (lane 5), bovine (lane 6), rabbit (lane 7) and chicken (lane 8) ranging from 14 Kb to 3.0 Kb. There is no detectable hybridization with the yeast DNA (lane 9). These results indicate that there are notable homologies among the genes encoding p80 in various species.

2. Sequencing of Kcal 1.6

DNA sequencing is performed using the "Taq-Track" sequencing system (Promega Corp.) or the "Sequenase" system (U.S. Biochemical, Cleveland, Ohio). The nucleotide sequence obtained indicates that the clone is not full length, and lacks an initiation methionine residue. To obtain a full-length clone, Kcal 1.6 is used as a probe to screen the original porcine aorta cDNA library. Positive clones are analyzed by restriction mapping and electrophoresis for relatedness and insert size. One cDNA clone (designated Kcal 1.8) which is slightly longer than Kcal 1.6 is isolated and sequenced. The nucleotide and amino acid sequence of Kcal 1.8 is shown in FIGS. 3A–3E. The cDNA encodes 437 amino acids, the hydropathy plot (FIG. 4) indicates four strongly hydrophobic putative transmembrane domains. There is a putative calcium binding domain which closely matches that of the cloned cDNA slo encoding a putative calcium activated K-channel in Drosophila. However, there is no significant sequence homology between Kcal 1.8 and slo in other regions.

There is one strong consensus sequence in Kcal 1.8 for the cAMP dependent protein kinase, as well as those putative casein kinase phosphorylation sites. The Kcal 1.8 sequence has no significant homologies with any known voltage gated K-channels, sodium channels or calcium channels.

3. Expression of Kcal 1.8

CV-1 cells (ATCC CCL70) stably expressing the Kcal 1.8 gene product are produced by introducing the cDNA in the stable mammalian expression plasmid, pRc/CMV (InVitrogen) which contains a Neo$^r$ marker. The Kcal 1.8 sequence is extracted from the pBluescript vector by digestion, with EcoRI and XhoI, and ligated into the corresponding sites of pRc/CMV. To transfect the cells, confluent 100 mm dishes of CV-1 cells are split and replated the day before the transfection, to ensure the cells are in log-growth phase. For electroporation, cells are harvested with trypsin, washed once with phosphate-buffered saline, and twice with an isotonic, low ionic strength buffer containing 272 mM sucrose, 7 mM sodium phosphate, pH 7.4 and 1 mM $MgCl_2$ (buffer E). The cells are resuspended in this same buffer to a final concentration of $1.5 \times 10^6$ cells/ml. Twenty µg of the appropriate vector are digested with 40 units of ScaI for 2 hours at 37° C. to linearize the plasmid. The linearized plasmid is phenol/chloroform extracted, EtOH precipitated, and resuspended in 400 µl of Buffer E. The resuspended DNA is mixed with 400 ul of CV-1 cells ($1 \times 10^6$ cells) and incubated at room temperature for 2 minutes prior to electroporation. Electroporation is accomplished using a Bio-Rad gene pulser with a 300-V pulse at 25 µFarads. Transfections are done in duplicate. The suspension is allowed to further incubate for 5 minutes at room temperature, and then plated onto 100 mm tissue culture dishes with 10 mls of Dulbecco's modified Eagle's medium containing 10% fetal calf serum. Two days following transfection, G418 is added to a final concentration of 200 ug/ml. When isolated G418-resistant colonies are identified, they are selected with cloning cylinders and amplified.

Transfected cells are harvested and washed. They are incubated with [$^{125}$I]apamin in the binding buffer "B": Tris-HCl 10 mM, KCl 10 mM, pH 7.4, in the presence or absence of 1 uM cold apamin. The incubation is at 4° C. for 30 minutes with cold apamin, followed by 1 hour incubation at 4° C. with [$^{125}$I]apamin (20,000 cpm/well). Target cells are then filtered and washed with the binding buffer plus BSA. The filters are counted in a gamma counter.

As shown in FIG. 5, Transfectant #1, 3, 10 and 12 show significantly enhanced binding of [$^{125}$I]apamin, compared to other transfectants shown.

REFERENCES

1. Rudy, B., *Neuroscience*, 25:729–749, 1988.

2. Halliwell, J. V., In Cook, N. S. (Ed.), *Potassium Channels; Structure, Classification, Function and Therapeutic Potential*, Ellis Horwood Ltd., 348–372, 1990.

3. Castle, N. A., Haylett, D. G., and Jenkinson, D. H., *TINS*, 1259–65, 1989.

4. Haylett, B. G. and D. H. Jenkinson, In Cook, N. S. (Ed.), *Potassium Channels; Structure, Classification, Function and Therapeutic Potential*, Ellis Horwood Ltd., 70–95, 1990.

5. Latorre, R., Oberhauser, A., Labarca, P. and Alvarez, O., *Annu. Rev. Physiol.*, 51:385–399, 1989.

6. Pennefather, P., Lancaster, B., Adams, P. and Nicoll, R. A., *Proc. Nat. Acad. Sci., USA* 82:3040–3044, 1985.

7. Marty, A., *TINS*, 12:420–424, 1989.

8. Lancaster, B., Nicoll R. A. and Perkel, D. J., *J. Neurosci.*, 11:23–30, 1991.

9. Strong, P. N., *Pharmac. Ther.*, 46137–162, 1990.

10. Saunders, H. H. and Farley, J. M., *J. Pharmacol. Exp. Ther.*, 257:1114–1119, 1991.

11. Moczydlowski, E. , Lucchesi, K. and Ravindran, A. , *J. Membrane Biol.*, 105:95–111, 1988.

12. Blatz, A. L. and Magleby, K. L., *J. Gen. Physiol.*, 84:1–23, 1984.

13. Blatz, A. L. and Magleby, K. L., *Nature*, 323:718–720, 1986.

14. Blatz, A. L. and Magleby, K. L., *TINS*, 10:463–467, 1987.

15. Habermann, E. and Fischer, K., *Eur. J. Biochem.*, 94:355–364, 1979.

16. Mourre, C., Hugues, M. and Lazdunski, M., *Brain Res.*, 382:239–249, 1986.

17. Seagar, M. J., Labbe-Jullie, C., Granier, C., Goll, A., Glossmann, H., Van Rietschoten, J. and Couraud, F., *Biochemistry*, 25:4051–4057, 1986.

18. Seagar, M. J., Marqueze, B. and Couraud, F., *J. Neurosci.*, 7:565–570, 1987.

19. Schmid-Antomarchi, H., Hugues, M., Norman, R., Ellory, C., Borsotto, M. and Lazdunski, M., *Eur. J. Biochem.*, 1421–6, 1984.

20. Wu, K., Carlin, R., Sachs, L. and Siekevitz, P., *Brain Res.*, 360:183–194, 1985.

21. Seagar, M. J., Labbe-Jullie, C., Granier, C., Van Rietschoten, J., Couraud, F., *J. Biol. Chem.*, 260:3895–3898, 1985.

22. Leveque, C., Marqueze, B., Couraud, F. and Seagar, M., *FEBS Letters*, 275:185–189, 1990.

23. Marqueze, B., Seagar, M. J., Couraud, F., *Eur. J. Biochem*, 169:295–298, 1987.

24. Laemmli, U. K., *Nature*, 227:680–685, 1970.

25. Ziai, M. R., Imberti, L., Nicotra, M. R., Badaracco, G., Segatto, O., Natali, P. G. and Ferrone, S., *Cancer Res.*, 47:2474–2480, 1987.

26. Ziai, M. R., Imberti, L., and Ferrone, S., *Immunol. Methods*, 82:233–241, 1985.

27. Hayashibe, K., Sassano, D., and Ziai, M. R., *J. Immunoassay*, 11:89–95, 1990.

28. Ohandra, M. and Frith, C. H., *Toxicol. Pathol.*, 19:164–167, 1991.

29. Staros, J. V., Wright, R. W., and Swingle, D. M., *Analyt. Biochem.*, 156:220–222, 1986.

30. Vaitukatis, J. L., *Methods in Enzymology*, 73:46–52, 1981.

31. Hsu, H. T, Wang, Y. C., Lawson, R. H., Wang, M. and Gonsalves, D., *Phytopathol.*, 80:158–162, 1990.

32. Cornett, W. C., Vincent, J. W., Gray, W. A., and Falkler, Jr., W. A., *J. Immunol. Methods*, 84:321–326, 1985.

33. Zweifach, A., Desir, G. V., Aronson, P. S., and Giebisch, G. H., *Amer. J. Physiol.*, 261:F187–F196, 1991.

34. Laskowski, F. M., Christine, C. W., Gitter, A. H., Beyenbach, K. W., Gross, P. and Froemter, E., *Renal Phys. Biochem.*, 13:70–81, 1990.

35. Cornejo, M., Gurggino, S. E., Guggino, W. B., *J. Membr. Biol.*, 110:49–56, 1989.

36. Klaerke, D. A., Karlish, S. J. D., Jorgenson, P. L., *J. Membr. Biol.*, 95:105–112, 1987.

37. Lu, L., Montrose-Rafizadeh, C. and Giggino, W. B., *J. Biol. Chem.*, 265:16190–16194, 1990.

38. Wang, W., Sackin, H., Giebisch, G., *Annu. Rev. Physiol.*, 54:81–96, 1992.

39. Ikeda, M., Dewar, D. and McCulloch, J., *Brain Res.*, 567:51–56, 1991.

40. Atkinson, N. S., Robertson, G. A. and Ganetzky, B., *Science*, 253:551–555, 1991.

41. Daniel, S., Malkowitz, L., Wang, H-C, Beer, B. and Ziai, M. R., *J. Pharmacol. Methods*, 25:185–193, 1991.

42. Messier, C., Mourre, C., Bontempi, B., Sif, J., Lazdunski, M. and Destrade, C., Brain Res., 551:322–326, 1991.

What we claim is:

1. A method for identifying a compound which is capable of modulating apamin receptor activity comprising contacting a compound or mixture of compounds with a host cell transformed or transfected with an oligonucleotide comprising a nucleic acid encoding porcine apamin binding protein, wherein the nucleic acid hybridizes under medium stringency conditions with a nucleic acid encoding the amino acid sequence of SEQ ID NO: 2, and observing the presence or absence of an effect on the host cell's ability to bind apamin.

2. The method of claim 1, wherein the oligonucleotide comprises a nucleic acid having the sequence of SEQ ID NO: 1.

3. A method for identifying a compound which is capable of modulating channel activity which comprises contacting a compound or a mixture of compounds with a host cell transformed or transfected with an oligonucleotide comprising a nucleic acid encoding porcine apamin binding protein, wherein the nucleic acid hybridizes under medium stringency conditions with a nucleic acid encoding the amino acid sequence of SEQ ID NO: 2, and observing the presence or absence of an effect on the host cell's ability to transport in a $^{86}$RB efflux assay.

4. The method of claim 3, wherein the oligonucleotide comprises a nucleic acid having the sequence of SEQ ID NO: 1.

* * * * *